United States Patent [19]

Sangokoya

[11] Patent Number: 5,391,529
[45] Date of Patent: Feb. 21, 1995

[54] SILOXY-ALUMINOXANE COMPOSITIONS, AND CATALYSTS WHICH INCLUDE SUCH COMPOSITIONS WITH A METALLOCENE

[75] Inventor: Samuel A. Sangokoya, Baton Rouge, La.

[73] Assignee: Albemarle Corporation, Richmond, Va.

[21] Appl. No.: 11,599

[22] Filed: Feb. 1, 1993

[51] Int. Cl.$^6$ .................... B01J 31/00; C08F 4/02
[52] U.S. Cl. .................... 502/103; 502/117; 502/158; 556/173
[58] Field of Search ............ 502/103, 117, 152, 129, 502/158; 556/173

[56] References Cited

U.S. PATENT DOCUMENTS

| | | | |
|---|---|---|---|
| 3,657,159 | 4/1972 | Vandenberg | 260/2 |
| 3,740,384 | 6/1973 | Ballard et al. | 260/94.9 |
| 3,969,332 | 7/1976 | Gloriod et al. | 502/103 X |
| 4,931,517 | 6/1990 | Fujita | 526/128 |
| 4,945,076 | 7/1990 | Piotrowski et al. | 502/117 |
| 5,017,714 | 5/1991 | Welborn, Jr. | 556/12 |
| 5,026,798 | 6/1991 | Canich | 526/127 |
| 5,034,549 | 7/1991 | Piotrowski et al. | 556/10 |
| 5,057,475 | 10/1991 | Canich et al. | 502/104 |
| 5,061,668 | 10/1991 | Hoxmeier et al. | 502/117 |
| 5,122,491 | 6/1992 | Kioka et al. | 502/117 |

FOREIGN PATENT DOCUMENTS 0129368  7/1989  European Pat. Off. .
0561476  9/1993  European Pat. Off. .

OTHER PUBLICATIONS

Siloxy–substituted Alumonoxanes: Synthesis from Polydialkylsiloxanes and Trimethylaluminum, and Application as Aluminosilicate Precursors, J. Mater. Chem. 1993, 3(6), 597–602, Landry, et al.

Ceram. Trans., 19 (Adv. Composite Matter.) 35–41 (1991), "Design and Synthesis of Polymeric Precursors to Aluminosilicates", by Allen W. Apblett, et al. (no month available).

Primary Examiner—Asok Pal
Attorney, Agent, or Firm—David M. Bunnell

[57] ABSTRACT

A siloxy-aluminoxane composition which is the reaction product of an alkyldisiloxane and an aluminoxane is provided. The compositions in combination with metallocenes of transition metals form catalysts which can be used in the polymerization of olefins such as ethylene.

20 Claims, No Drawings

SILOXY-ALUMINOXANE COMPOSITIONS, AND CATALYSTS WHICH INCLUDE SUCH COMPOSITIONS WITH A METALLOCENE

This process relates generally to soluble aluminoxane derivatives and more particularly to siloxy-aluminoxane compositions obtained by the reaction of alkyldisiloxanes and aluminoxanes which, in the presence of metallocenes, form catalytically active compositions for olefin polymerization.

U.S. Pat. No. 3,740,384 discloses that the addition of dihydroxysiloxane to non-metallocene organo-zirconium catalyst systems in the absence of aluminoxanes gave improved catalyst activity in olefin polymerization. Likewise, U.S. Pat. No. 4,945,076 describes the improved activity in olefin polymerization which is obtained by the addition of dihydroxysiloxane to a catalyst system consisting of a metallocene and an aluminoxane. The resulting ethylene polymer is said to have acquired a lower melt flow rate (MFR) than those produced without the silicon compound. U.S. Pat. No. 5,034,549 discloses that a preformed catalyst component is obtained by the reaction of dihydroxysiloxane or silicon diol with a zirconocene. The patent further alleges that this catalyst component, when used in conjunction with methylaluminoxane, formed a good catalyst system for olefin polymerization.

All the above mentioned disclosures describe the use of alkoxy-silanes having Si—O—C bonds, silicon diols having Si—OH bonds and dihydroxysiloxanes having both the Si—O—Si and Si—OH bonds. The reagents used in the present invention, namely alkyldisiloxanes, have only the Si—O—Si bonds. The chemical reactivity of the alkyldisiloxanes is significantly different from those of the silanols, silyl ethers, silyl esters and hydroxy disiloxanes (1. *Comprehensive Organometallic Chemistry*, Vol. 2,Chap. 9; Pergamon Press, 1982: 2. *Comprehensive Organic Chemistry*, Vol. 3, Chap. 13 Pergamon Press New York 1979). Those skilled in the art would appreciate the fact that silicon compounds having Si—OH bonds generally undergo dehydration and condensation reactions. These reactions are rarely observed in the case of alkyldisiloxanes. Thus, one could not anticipate any obvious similarity between the reactions of silanols, silyl ethers and silyl esters compared to alkyldisiloxanes. In fact one would not expect to isolate under similar conditions, the same product described in U.S. Pat. No. 5,034,549 by substituting an alkyldisiloxane for the dihydroxysiloxane or silicon diol, as this would require the breaking of Si—O bond which is more difficult than breaking the SiO—H bond.

It has now been found that aluminoxanes will react with alkyldisiloxanes to form novel, soluble siloxy-aluminum compounds which, in combination with metallocenes, provide olefin polymerization catalysts having very high activity.

In accordance with this invention there is provided a siloxy-aluminoxane composition which is the reaction product of an alkyldisiloxane and an aluminoxane where the molar portions of aluminum to alkyldisiloxane are from about 1:1 to 50:1.

Also provided is an olefin polymerization catalyst comprising a metallocene of a transition metal and a siloxy-aluminoxane composition which is the reaction product of an alkyldisiloxane and an aluminoxane where the molar portions of aluminum to alkyldisiloxane are from about 1:1 to 50:1.

Preferred aluminoxanes for use in making the siloxy-aluminoxane compounds are hydrocarbylaluminoxanes.

Hydrocarbylaluminoxanes may exist in the form of linear or cyclic polymers with the simplest compounds being a tetraalkylaluminoxane such as tetramethylaluminoxane, $(CH_3)_2AlOAl(CH_3)_2$, or tetraethylaluminoxane, $(C_2H_5)_2AlOAl(C_2H_5)_2$. The compounds preferred for use in olefin polymerization catalysts usually contain about 4 to 20 of the repeating units:

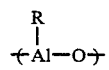

where R is $C_1$–$C_{10}$ alkyl and especially preferred are methylaluminoxanes (MAO). The methylaluminoxanes can contain some higher alkyl groups to improve their solubility. Such modified methylaluminoxanes are described, for example, in U.S. Pat. No. 5,157,008.

The aluminoxanes can be prepared as known in the art by the partial hydrolysis of trialkylaluminum compounds. The trialkylaluminoxane compounds can be hydrolyzed by adding either free water or water containing solids, which can be either hydrates or porous materials which have absorbed water. Because it is difficult to control the reaction by adding water per se, even with vigorous agitation of the mixture, the free water is preferably added in the form of a solution or a dispersion in an organic solvent. Suitable hydrates include salt hydrates such as, for example, $CuSO_4 \cdot 5H_2O$, $Al_2(SO_4)_3 \cdot 18H_2O$, $FeSO_4 \cdot 7H_2O$, $AlCl_3 \cdot 6H_2O$, $Al(NO_3)_3 \cdot 9H_2O$, $MgSO_4 \cdot 7H_2O$, $ZnSO_4 \cdot 7H_2O$, $Na_2SO_4 \cdot 10H_2O$, $Na_3PO_4 \cdot 12H_2O$, $LiBr \cdot 2H_2O$, $LiCl \cdot 1H_2O$, $LiI \cdot 2H_2O$, $LiI \cdot 3H_2O$, $KF \cdot 2H_2O$, $NaBr \cdot 2H_2O$ and the like and alkali or alkaline earth metal hydroxides such as, for example, $NaOH \cdot H_2O$, $NaOH \cdot 2H_2O$, $Ba(OH)_2 \cdot 8H_2O$, $KOH \cdot 2H_2O$, $CsOH \cdot 1H_2O$, $LiOH \cdot 1H_2O$ and the like. Mixtures of any of the above hydrates can be used. The mole ratios of free water or water in the hydrate to total alkyl aluminum compounds in the mixture can vary widely, such as for example from about 2:1 to 1:4 with ratios of from about 4:3 to 1:3.5 being preferred.

Such processes for preparing hydrocarbylaluminoxanes are described, for example, in U.S. Pat. No. 4,908,463. The methylaluminoxanes contain varying amounts, of from about 5 to 35 mole percent, of the aluminum value as unreacted trimethylaluminum.

The alkyldisiloxanes for use in the invention have alkyl groups which preferably contain from about 1 to 20 carbon atoms. The alkyldisiloxanes contain the Si—O—Si bond and are substantially free of Si—OH or Si—O—C bonds. The alkyl disiloxanes can contain mixed alkyl groups. Non-limiting examples of alkyldisiloxanes include hexamethyldisiloxane, hexaethyldisiloxane, tetramethyldisiloxane, and the like.

The siloxy-aluminoxane compositions can be prepared by reacting the aluminoxane and alkyldisiloxane in an organic solvent medium in molar portions of aluminum to alkyldisiloxane of from about 1:1 to 50:1. Mixtures of aluminoxanes and/or alkyldisiloxanes can be used in forming the compositions. Any inert organic solvent can be used as the reaction medium. Non-limiting examples of solvents include aliphatic hydrocarbons such as pentane, isopentane, hexane, cyclohexane, heptane, octane, decane, dodecane, hexadecane, octadecane and the like with those having carbon numbers of 5 to 10 being preferred and aromatic hydrocarbons such as benzene, toluene, xylene, cumene and the like with those having carbon numbers of 6 to 20 being preferred. Generally amounts of solvent to provide a total concentration of reactants of from about 10 to 30 wt. percent are used.

Preferred reaction temperatures range from about 25° to 90° C.

The siloxy-aluminoxane compounds can be used in combination with metallocenes to provide olefin polymerization catalysts. Such metallocenes are well known in the art and non-limiting examples include the metallocenes described in published European patent application No. 0 129,368 and U.S. Pat. Nos. 5,017,714 and 5,026,798, whose teachings with respect to such metallocenes are incorporated herein by reference. Illustrative examples of such metallocenes are bis-(cyclopentadienyl)-zirconium dimethyl, bis-(cyclopentadienyl)-zirconium dichloride, bis-(cyclopentadienyl)-zirconiummonochloride, bis-(cyclopentadienyl)titanium dichloride, bis-(cyclopentadienyl)-titanium difluoride, cyclopentadienyl-zirconium tri-(2-ethylhexanoate), bis-cyclopentadienyl)-zirconium hydrogen chloride, bis-(cyclopentadienyl)hafnium dichloride and the like.

The catalyst components are used in proportions to provide mole ratios of transition metal atom to aluminum atom of from about 0.0002:1 to 0.2:1 and preferably 0.0005:1 to 0.02:1. The catalyst components can be used in solution or deposited on a solid support. The solid support can be any particulate solid, and particularly porous supports such as talc or inorganic oxides, or resinous support material such as polyolefins. Preferably, the support material is an inorganic oxide in finely divided form.

Suitable inorganic oxide support materials which are desirably employed include Group IIA, IIIA, IVA or IVB metal oxides such as silica, alumina, silica-alumina and mixtures thereof. Other inorganic oxides that may be employed either alone or in combination with the silica, alumina or silica-alumina are magnesia, titania, zirconia, and the like. Other suitable support materials are finely divided polyolefins such as finely divided polyethylene.

The catalysts are effective to produce olefin polymers and especially ethylene polymers and ethylene/α-olefin copolymers. Examples of olefins that can be polymerized in the presence of the catalysts of the invention include α-olefins having 2 to 20 carbon atoms such as ethylene, propylene, 1butene, 1-hexene, 4-methyl-1-pentene, 1-octene, 1-decene, 1dodecene, 1-tetradecene, 1-hexadecene, and 1-octadecene. Polymerization of ethylene or copolymerization with ethylene and an α-olefin having 3 to 10 carbon atoms is preferable. Such polymerizations may be performed in either the gas or liquid phase (e.g. in a solvent, such as toluene, or in a diluent, such as heptane). The polymerization can be conducted at conventional temperatures (e.g., 0° to 120° C.) and pressures (e.g., ambient to 50 kg/cm$^2$) using conventional procedures as to molecular weight regulation and the like.

The invention is further illustrated by, but is not intended to be limited to, the following examples.

The following examples were carried out under inert atmosphere conditions, using Schlenk glassware and vacuum line, in conjunction with a N$_2$-drybox. Solvents were distilled using standard methods. Filtration and vacuum distillation were done inside a N$_2$-drybox and distillates were collected in a trap at −78° C. Disiloxanes were purchased from Aldrich and used without further purification. Aluminoxanes were obtained from stock solutions produced by Ethyl.

Example 1

Solid methylaluminoxanes (MAO, 38 mmol Al) was suspended in hexane (50 mL). The mixture was stirred at room temperature (30 minutes). Hexamethyldisiloxane (HMDS, 4.7 mmol) was then slowly added via syringe. After stirring for 16 hours, the mixture was filtered. The hexane solution was then concentrated to dryness by vacuum distillation. The resulting solid siloxy-MAO product contained 65% of the initial aluminum value. Silicon-29 and proton NMR showed one sharp singlet each for the siloxy group. Additionally, H-1 NMR showed the usual broad peak for methylaluminoxane in the aluminum alkyl region. The sharp signals suggest a probable end capping environment of the siloxy group in the MAO structure.

Example 2

Solid MAO (122 mmol Al) was suspended in hexane (300 mL) in a reaction flask. HMDS (60 mmol) was added via syringe. The mixture was stirred for about 30 minutes at room temperature and then heated to 70° C. (oil bath) for another 12 hours. The slurry was filtered and the filtrate was concentrated to give a white solid material which contained 67% of the initial aluminum value. Si-29 and H-1 NMR data are similar to those obtained for Example 1.

Example 3

Solid MAO (60 mmol Al) was placed in hexane (100 mL). To the slurry was added HMDS (75 mmol). The mixture was magnetically stirred for about 20 hours and then filtered. The filtrate was concentrated to give white granular siloxy-MAO derivative.

The preceding Examples 1–3 showed that the variation of HMDS concentration, reaction time and thermal conditions did not significantly alter either the product yield or the spectroscopic data of the resulting solid siloxy-MAO derivative.

Example 4

This preparation was done to investigate the effect of a mixed solvent system, toluene/hexane. A toluene solution of MAO (350 mmol Al) was placed in a reaction flask and hexane (150 g) was added. The HMDS (90 mmol) was then slowly added via syringe. The mixture was stirred for about 14 hours at room temperature. After filtration, the clear liquid which contained 90% of the original aluminum value, was concentrated to give a white solid siloxy-MAO product.

H-1 NMR data showed more sharp peaks overlapping the usual MAO broad peak in the aluminum alkyl region, than was seen in the alkane product.

Example 5

Solid MAO (30 mmol Al) was dissolved in toluene (20 mL) and then HMDS (5 mmol) was added. The reaction was carried out as described in Example 1. The resulting solid product contained 92% of the original aluminum value. H-1 NMR contained several singlet peaks buried under the usual broad MAO peak.

Example 6

Solid MAO (75 mmol Al) was added to a toluene solvent (50 mL). To this solution was then added HMDS (30 mmol) from a syringe. The mixture was stirred at room temperature for about 4 hours. The hexane (50 mL) was added and the mixture was stirred for another 2 hours and filtered. The filtrate was concentrated to dryness to give a solid product which contained 85% of the initial aluminum value.

The H-1 NMR of the solid, hexane derived siloxy-MAO product showed only one sharp singlet peak in the aluminum alkyls region regardless of the concentration of HMDS. By contrast, similar spectra for the solid, MAO in toluene derived products showed several sharp singlet peaks in the aluminum alkyls region. Furthermore, as the molar ratio of HMDS increased the number of singlet peaks attributable to the siloxy derivatives increased. The reason for this unequivocal solvent effect is not known.

Example 7

Solid MAO (75 mmol Al) was dissolved in toluene (50 mL). To this solution was added HMDS (75 mmol). The mixture was stirred at room temperature for about 20 hours. Hexane (50 mL) was added and then the mixture was stirred for another 4 hours. After filtration and concentration, the resulting solid siloxy-MAO compound contained 88% of the original aluminum value.

H-1 NMR of the solid compound showed several singlet peaks ($Me_3SiO$) buried under the broad MAO peaks.

The starting material in the above described reactions was solid MAO. This was obtained by removal of toluene from the MAO solution via vacuum distillation. For commercial purposes, it is desirable to avoid extra processing requirements. The following examples describe the formation of siloxy-MAO compositions directly from the initial toluene solution of MAO.

Example 8

A MAO solution in toluene (271 mmol Al, 78 g of a 9.4% Al by weight solution) was placed in a reaction flask. HMDS (68 mmol) was slowly added at room temperature. The mixture was stirred for about 12 hours and then heat (oil bath, 80° C.) was applied for about 2 hours. The mixture was filtered and the filtrate was found to contain 92% of the original aluminum value.

This siloxy-MAO solution was found to be more active, compared to the original MAO solution, in an ethylene polymerization test (Table 1).

Example 9

To a solution of MAO in toluene (300 mmol Al) was added HMDS (150 mmol). The reaction was carried out as described in Example 8. The filtrate contained 93% of the original aluminum value. The resulting siloxy-MAO solution was found to be very active in ethylene polymerization (Table 1).

Example 10

A MAO solution in toluene (272 mmol Al) was placed in a reaction flask. HMDS (204 mmol) was slowly added from a syringe. The reaction was carried out as described in Example 8. The resulting filtrate contained about 82% of the original aluminum value. A significant reduction in the trimethylaluminum (TMA) content (from 30% TMA to 13% TMA) was observed for this product.

The product in conjunction with zirconocene dichloride is highly active in ethylene polymerization (Table 1).

Example 11

A solution of MAO in toluene (272 mmol Al) was treated with HMDS (272 mmol). The reaction was carried out as described in Example 8. About 86% of the original aluminum value was recovered after filtration. The liquid product was found to be very active in ethylene polymerization (Table 1).

Example 12

MAO solution (194 mmol Al) was allowed to react with hexaethyldisiloxane (HEDS, 38.8 mmol). The reaction was carried out as described in Example 8. The resulting filtrate contained 79% of the original aluminum value.

A portion of the filtrate was concentrated under vacuum to give an oily product.

Example 13

A solution of isobutylaluminoxane (IBAO, 109 mmol Al) in cyclohexane was treated with HMDS (27 mmol). The mixture was stirred at room temperature for about 2 hours and then heated (oil bath) at 100° C. for another 10 hours. The clear solution was concentrated under vacuum to give a thick oily product. Ordinarily, a solid product would have resulted after similar treatment of the original IBAO solution. H-1 NMR showed broad peaks from 0.2 to 0.4 ppm which is attributable to the siloxy-aluminoxane group. All the other IBAO peaks are still present.

Polymerization

Ethylene polymerization was conducted in a Parr reactor (600 mL) equipped with a cooling coil, magnetic stirrer, pressure gauge and a gas inlet. The catalyst system, siloxy-MAO and zirconocene dichloride, are dissolved in toluene (300 mL). The loading was done in a dry-box after which the reactor was assembled in a well vented hood. Ethylene was passed into the reactor at 60 psi for 10 minutes while the temperature was maintained at about 90° C.

After cooling down to room temperature, the reactor contents were poured into a beaker where an equal volume of methanol was added to destroy the catalyst system. The polyethylene was collected by filtration and then dried in a vacuum oven.

Examples 14 and 15

Solid samples obtained from Examples 1 and 5 were separately employed in conjunction with zirconocene dichloride to conduct ethylene polymerization tests as described above. Results are shown in Table 1.

Examples 16 to 19

Toluene samples of the siloxy-aluminoxanes obtained respectively from Examples 8 to 11 were separately employed in the presence of zirconium dichloride to conduct ethylene polymerization as described above. Results are shown in Table 1.

Comparison

A comparative polymerization was carried out using regular methylaluminoxane (MAO) solution in toluene (9.4 wt. % Al) in conjunction with zirconocene dichloride without the addition of disiloxane. The results are shown in Table 1.

Table 1 shows that no significant additional activity was gained as the molar ratio of HMDS was increased.

However, the data in this table show a notable increase (about 50%) in the activity of the siloxy-MAO derivatives as compared to the regular MAO under similar conditions.

TABLE 1

| | | | Siloxy-MAO Derivatives/Ethylene Polymerization[a] | | | | |
|---|---|---|---|---|---|---|---|
| Example # | (%) HMDS[d] | Aluminum (Moles × $10^{-3}$) | Zirconocen Dichloride (Moles × $10^{-6}$) | Al/Zr Mole Ratio | Activity (× $10^6$) g(PE)/mol.Zr · atm · hr | Activity Compared to Regular MAO | PE (g) |
| 14 | 15 | 16.7 | 12.4 | 1347 | 4.74 | NA[b] | 40 |
| 15 | 15 | 16.7 | 12.4 | 1347 | 4.98 | NA[b] | 42 |
| 16 | 25 | 10 | 6.8 | 1470 | 10.16 | 1.8 | 47 |
| 17 | 50 | 10 | 6.8 | 1470 | 9.74 | 1.7 | 45 |
| 18 | 75 | 10 | 6.8 | 1470 | 9.08 | 1.6 | 42 |
| 19 | 100 | 10 | 6.8 | 1470 | 9.08 | 1.6 | 42 |
| Comparison | Regular MAO | 10 | 6.8 | 1470 | 5.62 | 1[c] | 26 |

[a]Conducted at 60 psi ethylene, 90° C., in toluene (300 mL) for 10 minutes.
[b]NA → Not applicable, because the Al/Zr ratio is different.
[c]Control experiment using standard regular MAO solution in toluene.
[d]15% HMDS is defined as the product obtained from 100 mmol Al/15 mmol HMDS.

What is claimed is:

1. A siloxy-aluminoxane composition comprising the reaction product of an alkyldisiloxane, which is substantially free of Si—OH or Si—O—C bonds, and an aluminoxane, where said alkyldisiloxane and said aluminoxane are reacted in an organic solvent at a temperature of from about 25° to 100° C. and the molar portions of aluminum to alkyldisiloxane are from about 1:1 to 50:1.

2. The composition of claim 1 wherein the alkyl groups in said alkyldisiloxane have from about 1 to 20 carbon atoms and said aluminoxane is a hydrocarbylaluminoxane wherein the hydrocarbyl groups contain from about 1 to 10 carbon atoms.

3. The composition of claim 2 wherein said alkyldisiloxane is hexamethyldisiloxane and said hydrocarbylaluminoxane is methylaluminoxane.

4. The composition of claim 2 wherein said alkyldisiloxane is hexaethyldisiloxane and said hydrocarbylaluminoxane is methylaluminoxane.

5. The composition of claim 2 wherein said alkyldisiloxane is hexamethyldisiloxane and said hydrocarbylaluminoxane is butylaluminoxane.

6. The composition of claim 2 wherein said alkyldisiloxane is hexaethyldisiloxane and said hydrocarbyl aluminoxane is butylaluminoxane.

7. An olefin polymerization catalyst comprising a metallocene of a transition metal and a siloxy-aluminoxane composition which is the reaction product of an alkyldisiloxane, which is substantially free of Si—OH or Si—O—C bonds, and an aluminoxane where said alkyldisiloxane and said aluminoxane are reacted in an organic solvent at a temperature of from about 25° to 100° C. and the molar portions of aluminum to alkyldisiloxane are from about 1:1 to 50:1.

8. The catalyst of claim 7 which contains mole ratios of transition metal atom in said metallocene to aluminum atom in said siloxy-aluminoxane composition of from about 0.0002:1 to 0.2:1.

9. The catalyst of claim 7 which contains mole ratios of transition metal atom in said metallocene to aluminum atom in said siloxy-aluminoxane composition of from about 0.0005:1 to 0.02:1.

10. The catalyst of claim 7 wherein the alkyl groups in said alkyldisiloxane have from about 1 to 20 carbon atoms and said aluminoxane is a hydrocarbylaluminoxane wherein the hydrocarbyl groups contain from about 1 to 10 carbon atoms.

11. The catalyst of claim 10 wherein said alkyldisiloxane is hexamethyldisiloxane and said hydrocarbylaluminoxane is methylaluminoxane.

12. The catalyst of claim 10 wherein said alkyldisiloxane is hexaethyldisiloxane and said hydrocarbylaluminoxane is methylaluminoxane.

13. The catalyst of claim 10 wherein said alkyldisiloxane is hexamethyldisiloxane and said hydrocarbylaluminoxane is butylaluminoxane.

14. The catalyst of claim 10 wherein said alkyldisiloxane is hexaethyldisiloxane and said hydrocarbyl aluminoxane is butylaluminoxane.

15. The catalyst of claim 10 which contains mole ratios of transition metal in said metallocene to aluminum atom in said siloxy-aluminoxane composition of from about 0.0002:1 to 0.2:1.

16. The catalyst of claim 10 which contains mole ratios of transition metal in said metallocene to aluminum atom in said siloxy-aluminoxane composition of from about 0.0005:1 to 0.02:1.

17. The composition of claim 1 wherein said reaction product is a filtered reaction product.

18. The catalyst of claim 7 wherein said reaction product is a filtered reaction product.

19. The composition of claim 2 wherein said alkyldisiloxane is tetramethyldisiloxane and said hydrocarbylaluminoxane is methylaluminoxane.

20. The catalyst of claim 10 wherein said alkyldisiloxane is tetramethyldisiloxane and said hydrocarbylaluminoxane is methylaluminoxane.

* * * * *